United States Patent
Von Wieding et al.

(10) Patent No.: US 10,123,830 B2
(45) Date of Patent: *Nov. 13, 2018

(54) HYBRID BONE PLATE

(71) Applicant: Stryker European Holdings I, LLC, Kalamazoo, MI (US)

(72) Inventors: Holger Von Wieding, Kiel (DE); Rose Riemer, Solothurn (CH); Michel Grimm, Olten (CH); Jörg Schneider, Solothurn (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/457,015

(22) Filed: Mar. 13, 2017

(65) Prior Publication Data

US 2017/0181783 A1    Jun. 29, 2017

Related U.S. Application Data

(63) Continuation of application No. 13/258,854, filed as application No. PCT/EP2009/054193 on Apr. 8, 2009, now Pat. No. 9,622,800.

(51) Int. Cl.
*A61B 17/80* (2006.01)
*A61B 90/00* (2016.01)

(52) U.S. Cl.
CPC .......... *A61B 17/8061* (2013.01); *A61B 17/80* (2013.01); *A61B 17/8023* (2013.01);
(Continued)

(58) Field of Classification Search
CPC . A61B 17/80; A61B 17/8004; A61B 17/8009; A61B 17/8014; A61B 17/8019;
(Continued)

(56) References Cited

U.S. PATENT DOCUMENTS 4,794,231 A    12/1988   Banas et al.
5,925,268 A    7/1999   Britnell
(Continued)

FOREIGN PATENT DOCUMENTS

CN          1694653 A    11/2005
DE    102006006341 A1    8/2007
(Continued)

OTHER PUBLICATIONS

International Search Report for PCT/EP2009/054193 dated Jul. 21, 2009.
RMI Titanium Company, "Titanium Alloy Guide", Jan. 2000, p. 6-7.

*Primary Examiner* — Kevin T Truong
*Assistant Examiner* — Tracy Kamikawa
(74) *Attorney, Agent, or Firm* — Lerner, David, Littenberg, Krumholz & Mentlik, LLP

(57) ABSTRACT

A hybrid bone plate has a first plate portion, having a first top surface and a first bottom surface and comprises a hard titanium alloy. A second plate portion has a second top surface and a second bottom surface and comprises a pure titanium or a soft titanium alloy. The first plate portion has a higher material yield strength than the second plate portion. The first plate portion and the second plate portion are connected to each other at a transition region by for example welding wherein in the transition region the first top surface and the second top surface together form a closed top integral surface and the first bottom surface and the second bottom surface together form a closed bottom integral surface.

12 Claims, 2 Drawing Sheets

(52) U.S. Cl.
CPC ....... *A61B 17/8047* (2013.01); *A61B 17/8057* (2013.01); *A61B 17/8085* (2013.01); *A61B 2090/0813* (2016.02)

(58) Field of Classification Search
CPC ............ A61B 17/8023; A61B 17/8028; A61B 17/8033; A61B 17/8038; A61B 17/8042; A61B 17/8047; A61B 17/8052; A61B 17/8057; A61B 17/8061; A61B 17/8071; A61B 17/8076; A61B 17/808; A61B 17/8085; A61B 17/809; A61B 17/8095
See application file for complete search history.

(56) References Cited

U.S. PATENT DOCUMENTS

| | | | |
|---|---|---|---|
| 6,293,949 | B1 | 9/2001 | Justis et al. |
| 6,436,502 | B1 | 8/2002 | Swift et al. |
| 6,955,677 | B2 * | 10/2005 | Dahners ............. A61B 17/8057 606/281 |
| 7,001,389 | B1 | 2/2006 | Navarro et al. |
| 7,189,237 | B2 | 3/2007 | Huebner |
| 9,622,800 | B2 * | 4/2017 | Von Wieding ......... A61B 17/80 |
| 2004/0073218 | A1 | 4/2004 | Dahners |
| 2004/0111089 | A1 | 6/2004 | Stevens et al. |
| 2005/0049595 | A1 | 3/2005 | Suh et al. |
| 2005/0182408 | A1 | 8/2005 | Pfefferle et al. |
| 2006/0065643 | A1 | 3/2006 | Hackius et al. |
| 2006/0079900 | A1 | 4/2006 | Mathieu et al. |
| 2006/0241618 | A1 | 10/2006 | Gasser et al. |
| 2007/0239158 | A1 | 10/2007 | Trieu et al. |
| 2009/0222050 | A1 | 9/2009 | Wolter et al. |

FOREIGN PATENT DOCUMENTS

| | | |
|---|---|---|
| GB | 2405342 A | 3/2005 |
| JP | 2009533170 A | 9/2009 |
| WO | 2004069066 A1 | 8/2004 |
| WO | 2007090543 A1 | 8/2007 |
| WO | 2007121080 A2 | 10/2007 |

* cited by examiner

HYBRID BONE PLATE

CROSS-REFERENCE TO RELATED APPLICATIONS

This application is a continuation of U.S. application Ser. No. 13/258,854, filed Dec. 9, 2011, now U.S. Pat. No. 9,622,800, which claims priority from National phase Entry under 35 U.S.C. § 371 of International Application Number PCT/EP2009/054193, filed Apr. 8, 2009, published in English as WO 2010/115458 on Oct. 14, 2010, the disclosures of which are hereby incorporated herein by reference.

BACKGROUND OF THE INVENTION

The present invention relates to a hybrid bone plate, and in particular to a hybrid bone plate, which allows for a more flexible application for a wide variety of bone geometries.

Bone plates are used for osteosynthesis applications, in particular for several kinds of fractures of bones. For this purpose, a wide variety of different bone plate geometries have been provided in order to meet the individual bone geometry and fracture situation of the patients to be treated.

To allow a flexible application of a bone plate, several approaches have been made, in order to allow a flexible orientation of for example screws for fixing the bone plate to the bone. For example, particularly designed threads have been provided in bore holes of a bone plate which allow for a variety of orientations of a bone screw when mounted to the bone and the bone plate. Further, bone plates have been proposed including inserts of an elastic material, which inserts were press-fitted into openings of the bone plate or by means of thread connections wherein such inserts also allow an application of the bone screws in different angles within a certain range. However, most of the previously known approaches do not allow a sufficient sterilization owing to the complicated geometry of the bone plate in the area of the screw holes or a save application. The reasons therefore may be on the one hand cavities, fissures and micro-slots when press-fitting an insert into a bone plate opening. On the other hand a bone plate may be optimized with respect to stability so that when using bone plates without inserts and turning in bone screws directly into an opening of a hard bone plate, it is possible to obtain debris particles occurring when turning a bone screw immediately into a bore hole or threaded bore hole of a bone plate. In particular, this may happen when using bone screws of a material being not adapted to match the material of the bone plate.

BRIEF SUMMARY OF THE INVENTION

In view of the known prior art, it may be seen as an object of the present invention to provide for a hybrid bone plate allowing a higher flexibility with respect to individual bone geometries and at the same time an increased safety for the patient to be treated.

The object of the present invention is solved by the subject-matter of the independent claim, wherein further embodiments of the invention are incorporated in the dependent claims.

According to an exemplary embodiment of the invention, a bone plate comprises a first plate portion having a first top surface and a first bottom surface, a second plate portion having a second top surface and a second bottom surface, wherein the first plate portion having a higher material yield strength than the second plate portion, wherein the first plate portion and the second plate portion are connected to each other to form a transition region, wherein in the transition region the first top surface and the second top surface together form a closed top integral surface, and the first bottom surface and the second bottom surface together form a closed bottom integral surface, wherein the second plate portion is designed to be deformed over the first plate portion.

Thus, it is possible to join a first plate portion and a second plate portion so as to use the first plate portion having a higher material yield strength as a structural portion, wherein the second plate portion having a lower material yield strength serves for an individual adaption of the bone plate to the respective bone geometry of a patient to be treated. Owing to the top and bottom integral surfaces being formed in the transition region, a sufficient sterilization can be established, since an integral surface does not allow any penetration of impurities into greater depth of the bone plate. In particular, the first top surface transits into the second top surface to form a closed top integral surface, and the first bottom surface transits into the second bottom surface to form a closed bottom integral surface without any gaps and cavities allowing impurities to be established. Closed integral surfaces may for example established by a material fitting. Press-fitting for example does not form a closed integral surface, because the transition between the first plate portion and the second plate portion is only a press-fitting, but no material fitting so that a certain risk remains for cavities to accommodate impurities.

According to an exemplary embodiment of the invention, the first plate portion consists of a first material, in particular a homogeneous material, and the second plate portion consists of a second material, in particular a homogeneous material.

Thus, both, the first plate portion and the second plate portion each can be formed of a homogeneous material having known material properties like for example the material yield strength.

According to an exemplary embodiment of the invention, the second material is a pure titanium or a soft titanium alloy and the first material is a hard titanium alloy.

It should be understood that the soft titanium alloy has a lower material yield strength than the hard titanium alloy. At the same time, the hard titanium alloy has a higher material yield strength than the pure titanium. In general, titanium and titanium alloys are very suitable materials for medical applications, since titanium and titanium alloys are light weight and very resistant against corrosion. Providing the second material as pure titanium or a soft titanium alloy allows for a reliable material fitting to the first material which is a hard titanium alloy. It should be noted that hard titanium alloy means that it is harder than the soft titanium alloy.

According to an exemplary embodiment of the invention, the hard titanium alloy is a Ti6Al4V alloy.

The Ti6Al4V alloy is particularly suitable for medical applications in view of strength and stability.

According to an exemplary embodiment of the invention, the pure titanium is a grade 2 titanium.

With respect to the hard titanium alloy, the pure titanium grade 2 allows a deformation of the second plate portion over the first plate portion.

According to an exemplary embodiment of the invention, the transition region consists of the first material and the second material.

Thus, the transition region is formed by an alloy consisting of the first material and the second material. In particular, the transition region may have a varying content ratio of the first material and the second material in a transversal direction, so that close to the first plate portion the alloy comprises a higher amount of the first material than the second material, wherein the alloy of the transition region close to the second plate portion comprises a higher amount of the second material than the first material. Thus, a smooth transition can be established from the first plate portion to the second plate portion allowing a higher stability of the transition region.

According to an exemplary embodiment of the invention, the transition region is formed by a weld seam.

A weld seam is a reliable possibility to form an integral surface from the first top surface to the second top surface on the one hand and from the first bottom surface to the second bottom surface on the other hand. Further, a weld seam allows for a material fit between the first plate portion and the second plate portion without the need to add a further material. A weld seam further allows for a reliable connection between the first plate portion and the second plate portion also in a greater depth of the material, so that a reliable and stable connection can be established between the first plate portion and the second plate portion.

According to an exemplary embodiment of the invention, the weld seam is formed by a process out of a group, the group consisting of laser welding, pulsed laser welding, electron beam welding and pulsed electron beam welding.

The above-mentioned welding processes allow for a reliable joining of the first plate portion and the second plate portion to form a closed integral surface on both, the top and the bottom side of the bone plate. In particular, the morphology of the material beside the transition region can be kept substantially unchanged, so that the material properties of the first plate portion as well as the properties of the second plate portion substantially remain unamended after having applied the welding process.

According to an exemplary embodiment of the invention, the weld seam is welded from both, a connecting line between the first top surface and the second top surface, and a connecting line between the first bottom surface and the second bottom surface.

In particular, for bone plates having a certain thickness, a welding process from both sides of the bone plate, i.e. the abutment line between the first top surface and the second top surface on the one hand and the abutment line between the first bottom surface and the second bottom surface allows a reliable forming of a closed integral surface to avoid cavities. However, it should be noted that in particular for bone plates having a thinner dimension of the thickness, a weld seam process from only one side, top or bottom, may be sufficient for forming a closed integral surface on both, the top surface and the bottom surface.

According to an exemplary embodiment of the invention, the second portion is an insert.

An insert may be a kind of an annular portion for applying a bone screw. When providing an insert having a lower material yield strength than the remaining bone plate, it is possible by deforming the insert to align the direction of the bone screw according to need, so that by providing an insert having a lower material yield strength, the application of a bone plate, and in particular a bone screw and a bone plate may be adapted according to an individual geometry of a bone of a patient to be treated.

According to an exemplary embodiment of the invention, at least one of a connecting line between the first top surface and the second top surface, and a connecting line between the first bottom surface and the second bottom surface forms a closed loop.

Thus, in particular the second plate portion being made of the softer material can be circumferenced by the harder material of the first plate portion. Thus, the circumferencing portion of a material of a higher material yield strength may serve as a structural element keeping the outer contour of the bone plate substantially in a desired form or shape, wherein the inner portion, i.e. the second plate portion of a softer material or a material having a lower material yield strength, can be used for a geometric adaption to the individual bone geometry of the patient to be treated. Thus, in particular the form and shape stability of the outer contour or the outer edges of the bone plate can be maintained in a well-defined manner, so that an outer geometry of the bone plate can be maintained.

According to an exemplary embodiment of the invention, the first plate portion comprises a first wall portion and the second plate portion comprises a second wall portion, wherein the first wall portion and the second wall portion before a welding process are aligned to each other.

Thus, a kind of form-fitting can be established during the manufacturing process of the bone plate, which renders easier the manufacturing process of forming a closed integral surface, since a form-fit may avoid larger cavities during the manufacturing process. Further, it can be substantially avoided to form a concave transition portion when establishing the weld seam, since no additional material is used and the total volume to be filled maintains substantially unamended when providing a form-fitting of the first wall portion and the second wall portion.

According to an exemplary embodiment of the invention, both, the first wall portion and the second wall portion are formed as a cylindrical sector.

It should be noted that a cylindrical sector can be a circular cylindrical sector, but also a cylindrical sector of any other cross-sectional profile, like for example an elliptic cylinder or a free form cylinder.

It should be noted that the above features may also be combined. The combination of the above features may also lead to synergetic effects, even if not explicitly described in detail.

These and other aspects of the present invention will become apparent from and elucidated with reference to the embodiments described hereinafter.

BRIEF DESCRIPTION OF THE DRAWINGS

Exemplary embodiments of the present invention will be described in the following with reference to the following drawings.

DETAILED DESCRIPTION

Figure 1:
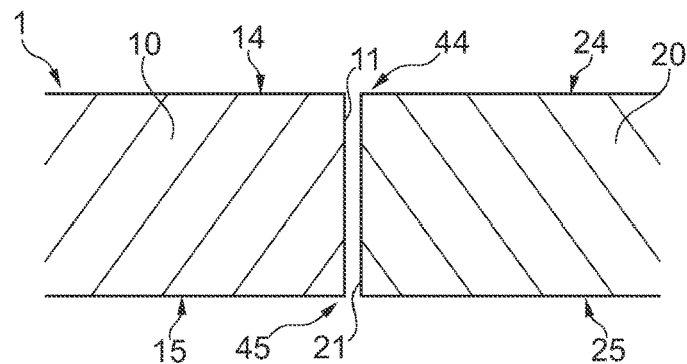
FIG. 1 illustrates a bone plate having a first plate portion and a second plate portion in an un-welded condition.

FIG. 1 illustrates a bone plate 1 having a first plate portion 10 and a second plate portion 20. The first plate portion 10 has a first top surface 14 and a first bottom surface 15. The second plate portion 20 has a second top surface 24 and a second bottom surface 25. FIG. 1 illustrates the first plate portion and the second plate portion in an unjoined or unwelded condition, wherein the both portions 10 and 20 are illustrated with a gap for sake of a clear illustration. However, it should be noted that the both plate portions 10 and 20 also in an unwelded condition may be positioned abutting to each other, so that a first wall portion 11 of the first plate portion 10 abuts to a second wall portion 21 of the second plate portion. The both top surfaces 14, 24 form a connecting line 44, wherein the both bottom surfaces 15 and 25 form a bottom connecting line. The material of the first plate portion has a higher material yield strength than the second plate portion 20. Thus, it is possible to deform the second plate portion 20 over the first plate portion 10, when the first plate portion 10 and the second plate portion 20 are joined or connected to each other, as will be described in the following with respect to FIGS. 2 and 3.

Figure 2:
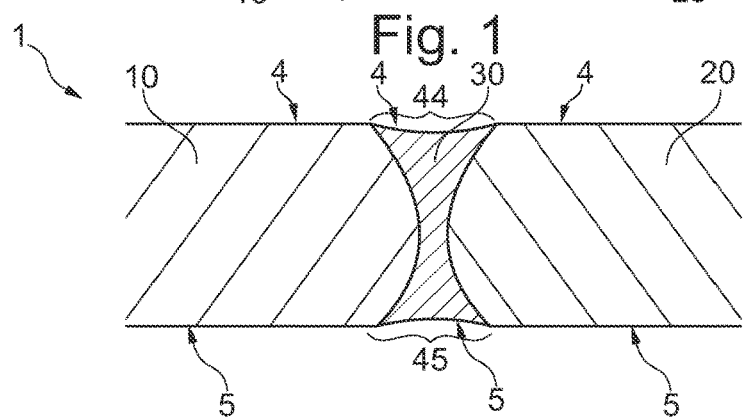
FIG. 2 illustrates a bone plate having a first plate portion and a second plate portion in a welded condition being welded from both sides.

FIG. 2 illustrates a first plate portion 10 and a second plate portion 20 of a bone plate 1 in a joined condition, which is illustrated as a welding joint. In a joined or welded condition, the bone plate 1 further comprises a transition region 30 joining the first plate portion 10 and the second plate portion 20. As a result, the bone plate 1 has a closed integral surface 4, which is formed by the first top surface and the second top surface on the one hand, and a bottom closed integral surface 5, which is formed by the both bottom surfaces 15 and 25. The connecting line in the welded condition has a width of the welding seam. It should be noted that the welding process can be carried out by a laser welding, a pulsed laser welding, an electron beam welding or a pulsed electron beam welding. Thus, the impact of the welding process can be limited to the transition region 30, so that the structural morphology of the first plate portion and the second plate portion 20 remains substantially unamended. This allows to also maintain the material properties of the first plate portion 10 and second plate portion 20 with respect to material yield strength, deformability, etc. It should be noted that the surface of the transition region 30 can be of a slight convex or concave shape, however, the surface of the transition region maintains the surface 4, 5 substantially as a closed integral surface in order to avoid cavities. Thus, it can be avoided that impurities can establish on or in the bone plate, and particular in the joining section or transition region 30.

FIG. 2 illustrates a joint of a bone plate 1, which is of a certain thickness, so that the welding process is carried out from both, the top surface as well as the bottom surface. Thus, the weld seam has substantially the form of an hour glass, i.e. being tapered from the bottom surface as well as from the top surface.

Figure 3:
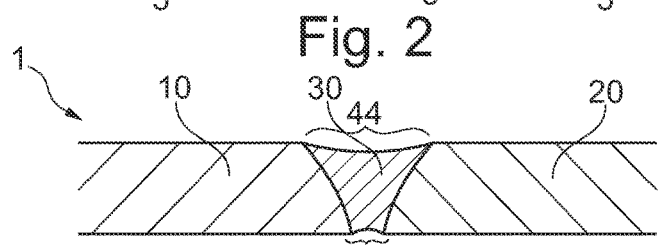
FIG. 3 illustrates a bone plate having a first plate portion and a second plate portion in a welded condition, being welded from one side.

It should be noted that for bone plates 1 having a lower thickness, the welding process can also be carried out from only one side, as illustrated in FIG. 3. In this case, the welding process is carried out from either the top or the bottom surface, so that the welding seam is substantially tapered from the top surface.

The welding region or transition region 30 is formed of an alloy consisting of the materials of both, the first plate portion 10 and the second plate portion 20. The first plate portion 10 as the plate portion having a higher material yield strength may be made of for example a hard titanium alloy, for example Ti6Al4V alloy, which had been established for medical application purposes in the past. The second plate portion 20 may be made of pure titanium, for example of titanium of a grade of 2, or a soft titanium alloy. Thus, it is possible to deform the second plate portion 20 over the first plate portion 10 in order to arrive at a geometric adaption to for example individual geometries of bones of patients to be treated.

Figure 4:
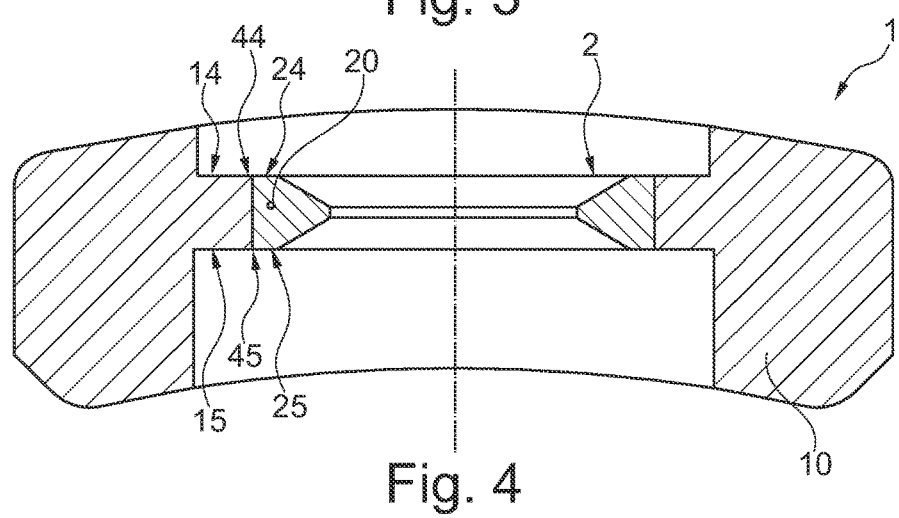
FIG. 4 illustrates a cross-sectional view of a bone plate with a frame body as a first plate portion and an insert as a second plate portion.

FIG. 4 illustrates a bone plate 1 wherein the first plate portion is a kind of frame, into which an insert is inserted as the second plate portion 20. FIG. 4 illustrates a schematic view of the bone plate 1 with the frame 10 and the insert 20 without further details of the transition region. An insert for example is used to allow to insert a bone screw and to allow a defined deformation of the insert, i.e. the second plate portion, wherein the first plate portion 10 as the bone plate frame substantially maintains the stability of the entire bone plate 1. However, the insert is not limited to be a circular insert, but may also be an elongated insert having different shapes. In particular an insert provides for a top connecting line 44 and a bottom connecting line 45 both of which form a closed loop. Thus, the second plate portion 20 is surrounded by the first plate portion 10 in order to maintain stability of the entire bone plate. However, in particular cases, it can be also useful to not provide such a stable outer contour, in order to have a more flexible bone plate portion, as will be described in further detail with respect to FIGS. 7 and 8.

The insert 2 of FIG. 4 allows to align a direction of a bone screw or to cut a thread into the material of the second bone plate as the insert 2. In particular, the material of an insert may be formed by a material which does not tend to form a splinter when screwing in a threaded screw.

Figure 5:
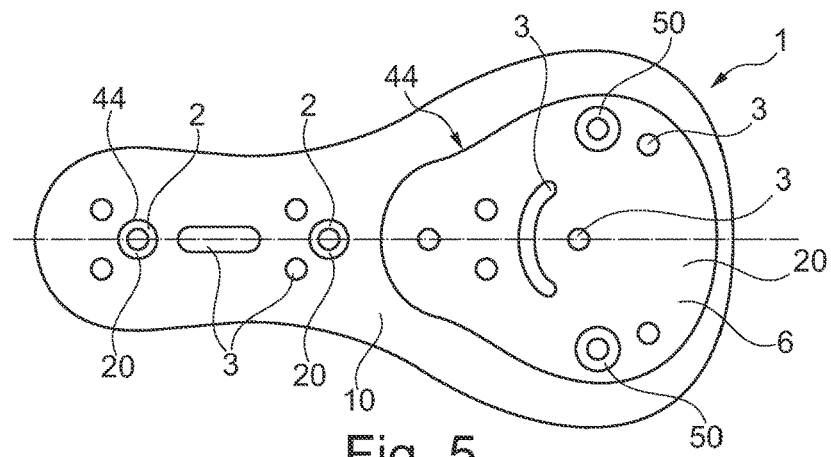
FIG. 5 illustrates a top view of a bone plate having a closed loop connecting line between the first plate portion and the second plate portion.

FIG. 5 illustrates a top view of a bone plate having both, inserts 2 having one central bore and an insular second plate portion 20 forming a larger insert region 6, which larger region allows for example a plurality of bore holes 3. The bore holes may be designed as circular bore holes or may also be designed as elongated holes or slot. In FIG. 5 all second plate portions 20 provide for a connecting line 44 as a closed loop.

Figure 6:
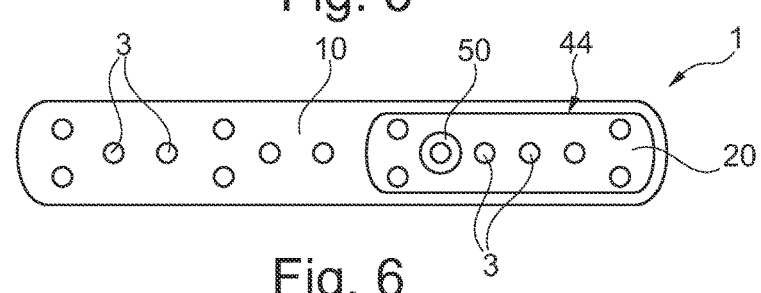
FIG. 6 illustrates a bone plate in an elongated form having a closed loop connecting line between a first plate portion and a second plate portion.

FIG. 6 illustrates a further embodiment of a bone plate 1, having a first plate portion 10 and a second plate portion 20. The first plate portion 10 circumferences the second plate portion 20 to provide a higher stability, in particular when the second plate portion is of a very low material yield strength requiring an external stabilization. Both, the first plate portion 10 and second plate portion can be provided with bore holes. It should be noted that within the second plate portion 20 having a lower material yield strength than the first plate portion 10, a further plate portion 50 can be provided. It may be useful to provide the further or third plate portion 50 with a material yield strength, which is lower than the material yield strength of the second plate portion 20. Thus, material of the second plate portion allows a rough adaption of a second plate portion, wherein a further third plate portion 50 having a further reduced material yield strength allows for a more detailed adaption of for example an aligning direction of a bone screw.

Figure 7:
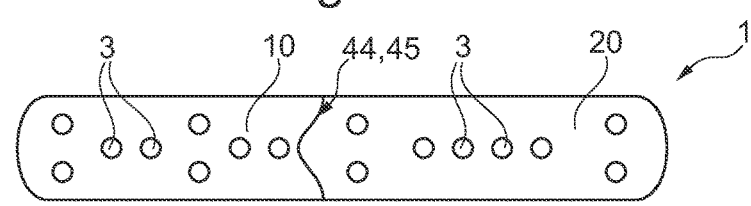
FIG. 7 illustrates an elongated bone plate having an open loop connecting line between the first plate portion and the second plate portion.

FIG. 7 illustrates a further exemplary embodiment of a bone plate 1, wherein the first plate portion 10 and the second plate portion 20 are connected to form a connecting line 44, 45. The connecting line 44, 45 in FIG. 7 extends to the outer contour of the entire bone plate 1, so that in the embodiment of FIG. 7, the first plate portion 10 does not circumference the second plate portion 20. Thus, a much more flexible adaption of the second plate portion 20 is possible.

Figure 8:
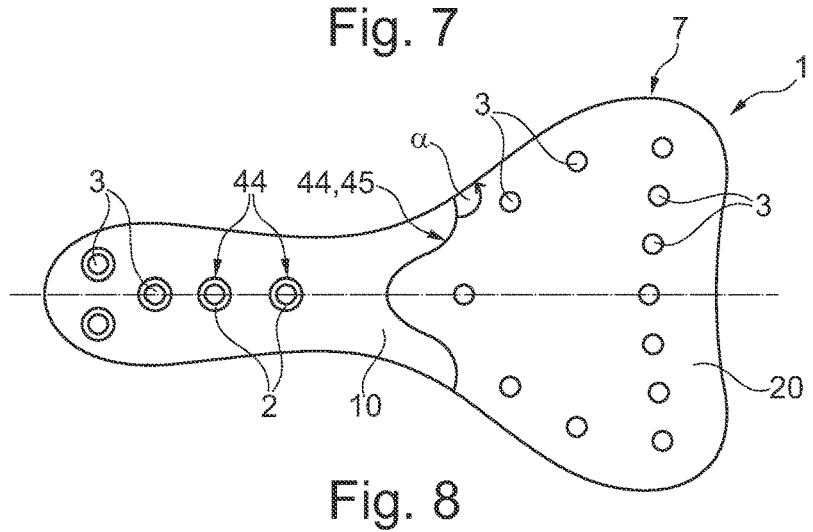
FIG. 8 illustrates a top view of a bone plate having an open loop connection line between the first plate portion and the second plate portion, and inserts in the first plate portion.

FIG. 8 illustrates a top view of a further exemplary embodiment of the invention, where the bone plate 1 comprises a first plate portion 10 and a second plate portion 20. The connecting line 44, 45 connecting the first plate portion and the second plate portion may be formed as a bended line, however, this connecting line may also be formed as a straight line, if needed. The angle formed by the outer contour 7 and the connecting line 44, 45 (angle α) may be between +/−45°, preferably of substantially 90°.

It should be noted that the term "comprising" does not exclude other elements or steps and the "a" or "an" does not exclude a plurality. Also elements described in association with different embodiments may be combined so as to form a synergetic effect.

It should be noted that reference signs in the claims shall not be construed as limiting the scope of the claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A longitudinally extending bone plate for implantation on a long bone having a shaft with an outwardly facing continuous surface, comprising:
    first and second ends, the bone plate having a first plate portion extending from the first end of the plate to the second end and having a first region forming the first end of the bone plate, the first plate portion having a first top surface and a first bottom surface, a first outwardly facing edge and is made entirely of a hard titanium alloy;
    a single second plate portion, having a second top surface and a second bottom surface adjacent the second end of the bone plate, a second outwardly facing edge, and the second plate portion is made entirely of pure titanium or a titanium alloy softer than the hard titanium alloy of the first plate portion and the first plate portion having a second region of hard titanium alloy completely surrounding the second plate portion, the first region of the first plate portion and the second plate portion each having a plurality of apertures extending from the top surface to the bottom surface thereof for receiving bone screws;
    wherein the entire first plate portion has a higher material yield strength than the entire second plate portion to allow for deformation of the second plate portion to conform to the long bone,
    wherein the first plate portion second region and the second plate portion are welded together and have curvilinear portions extending transverse to a central longitudinal axis of the bone plate to form a curvilinear weld line between the first and second plate portions where the first and second plate portions are connected together; and
    wherein the weld line extends completely between the outwardly facing edges of each plate portion, the first outwardly facing edge forms the entire outwardly facing continuous surface of the bone plate.

2. The bone plate as set forth in claim 1, wherein a first thickness defined by the first top surface and the first bottom surface and a second thickness defined by the second top surface and the second bottom surface are equal and the second top surface and the second bottom surface of the second portion are contiguous with the first top surface and the first bottom surface of the first portion, respectively.

3. The bone plate according to claim 1, wherein the hard titanium alloy is a Ti6Al4V alloy.

4. The bone plate according to claim 1, wherein the pure titanium is a grade 2 titanium.

5. The bone plate according to claim 1, wherein the weld is formed by a process selected from the group consisting of: laser welding, pulsed laser welding, electron-beam welding and pulsed electron-beam welding.

6. The bone plate as set forth in claim 5, wherein the weld extends from the top surfaces to the bottom surfaces of the first and second portions.

7. A longitudinally extending bone plate for implantation on a long bone having a shaft with an outwardly facing continuous surface, comprising:
    first and second ends, the bone plate having a first plate portion extending from the first end of the plate to the second end and having a first region forming the first end of the bone plate, the first plate portion having a first top surface and a first bottom surface, a first outwardly facing edge and is made entirely of a hard titanium alloy;
    a second plate portion, having a second top surface and a second bottom surface adjacent the second end of the bone plate, a second continuous outwardly facing edge, and the second plate portion is made entirely of pure titanium or a titanium alloy softer than the hard titanium alloy of the first plate portion and the first plate portion having a second region of hard titanium alloy completely surrounding the second plate portion, the first region of the first plate portion and the second plate portion each having a plurality of apertures within the respective outwardly facing edge extending from the top surface to the bottom surface thereof for receiving bone screws;
    wherein the entire first plate portion has a higher material yield strength than the entire second plate portion to allow for deformation of the second plate portion to conform to the long bone,
    wherein the first plate portion second region and the second plate portion are welded together and have curvilinear portions extending transverse to a central longitudinal axis of the bone plate to form a curvilinear weld line between the first and second plate portions where the first and second plate portions are connected together; and
    wherein the weld line extends completely between the outwardly facing edges of each plate portion, the first outwardly facing edge forms the entire outwardly facing continuous surface of the bone plate.

8. The bone plate as set forth in claim 7, wherein a first thickness defined by the first top surface and the first bottom surface and a second thickness defined by the second top surface and the second bottom surface are equal and the second top surface and the second bottom surface of the second portion are contiguous with the first top surface and the first bottom surface of the first portion, respectively.

9. The bone plate according to claim 7, wherein the hard titanium alloy is a Ti6Al4V alloy.

10. The bone plate according to claim 7, wherein the pure titanium is a grade 2 titanium.

11. The bone plate according to claim 7, wherein the weld is formed by a process selected from the group consisting of: laser welding, pulsed laser welding, electron-beam welding and pulsed electron-beam welding.

12. The bone plate as set forth in claim 11, wherein the weld extends from the top surfaces to the bottom surfaces of the first and second portions.

* * * * *